United States Patent [19]

Schubert et al.

[11] 4,035,477

[45] July 12, 1977

[54] PRESSURIZED FOAMING SHAVING COMPOSITION AND METHOD OF MAKING THE SAME

[75] Inventors: Warren R. Schubert, Somerset; Louis J. Literate, Iselin, both of N.J.

[73] Assignee: Colgate-Palmolive Company, New York, N.Y.

[21] Appl. No.: 559,969

[22] Filed: Mar. 19, 1975

Related U.S. Application Data

[63] Continuation of Ser. No. 300,578, Oct. 25, 1972, abandoned.

[51] Int. Cl.$^2$ .......................................... A61K 7/06
[52] U.S. Cl. ................................... 424/47; 424/73
[58] Field of Search ............. 424/73; 252/DIG. 13, 252/90

[56] References Cited

U.S. PATENT DOCUMENTS

| | | | |
|---|---|---|---|
| 2,192,907 | 3/1940 | Harris | 424/73 X |
| 2,968,628 | 1/1961 | Reed | 252/305 |
| 2,995,521 | 8/1961 | Estignard Bluard | 424/73 X |
| 3,240,396 | 3/1966 | Friedenberg | 252/DIG. 13 |
| 3,533,955 | 10/1970 | Pader et al. | 252/DIG. 13 |
| 3,574,118 | 4/1971 | Baker | 424/73 |
| 3,705,855 | 12/1972 | Marsehner | 424/73 |

OTHER PUBLICATIONS

Sagarin Cosmetics Science & Technology, 1957, p. 405.

*Primary Examiner*—Dale R. Ore
*Attorney, Agent, or Firm*—Steven J. Baron; Murray M. Grill; Herbert S. Sylvester

[57] ABSTRACT

A pressurized foaming shaving composition includes with an anionic surface active foaming agent and a foam stabilizer, in an aqueous medium, a mixture of higher fatty acid triglycerides of acids of 16 to 18 carbon atoms, which acids include stearic, oleic and palmitic acids, the proportion of saturated fatty acid groups to unsaturated fatty acid groups being about 1 or more, plus an organic liquefied gas propellant to pressurize the composition. The product made is of satisfactory foam characteristics, including body, and gives comfortable, clean shaves which leave the skin feeling soft and conditioned. The shaving composition is especially useful for the shaving of body areas, such as the neck, upper legs and axillae and of areas such as the axillae to which preparations which can have irritant effects, such as antiperspirants and deodorants, are sometimes subsequently applied.

13 Claims, No Drawings

PRESSURIZED FOAMING SHAVING COMPOSITION AND METHOD OF MAKING THE SAME

This is a continuation of application Ser. No. 300,578 filed Oct. 25, 1972 now abandoned.

This invention relates to pressurized shaving compositions. More particularly, it is of such compositions and methods for their manufacture, wherein there is included a particular mixture of higher fatty acid triglycerides which improve the quality of the shave, resulting in clean and comfortable, easy shaves which leave the skin shaved feeling soft and conditioned. The particular triglyceride mixture, when employed in described proportion, has no significant detrimental effect on the shaving cream and the foam made is of satisfactory characteristics, being stable and of good body or "stiffness". The manufacturing method of the invention allows the production of the described foaming shaving composition without any interfering reaction of other components or reagents with the triglyceride mixture.

During the many years in which soaps and shaving compositions containing them have been employed to aid in shaving, various efforts have been made to improve the quality of the shave obtained with their use. In recent years pressurized or aerosol shaving compositions and even self-heating aerosol shaves have been manufactured. Many of such compositions give a copious foam which maintains its form when applied to the face or other body areas, holding a source of mositure in contact with the hairs or whiskers to be shaved to soften them so that cutting with a sharp razor blade is facilitated. In the self-heating or thermal aerosol shave the heat generated also aids in softening of the hair. Sometimes the foam helps to hold the hair erect, which is also considered to aid in shaving it off. Great strides have recently been made in improving the cutting surfaces of razor blades, with first, the stainless blade and then, various other alloys, coatings, and platings on such blades being employed to make a smoother, sharper cutting edge to facilitate clean shaving. Yet, despite these advances there is still a significant demand for blades and shave creams of such properties that the users thereof will obtain even better shaves. Apparently, some shavers still experience pulling, cutting of the skin, irritation of the skin, undesirable tightness of the skin after shaving and pain when irritant or even non-irritant acidic compositions are applied to the shaved area. The present invention of an improved shaving composition results in excellent shaves which are smooth, close, clean and comfortable and the shaved skin is left feeling soft and conditioned. Fewer nicks or pulls are experienced, as is less irritation, and the skin is not as susceptible to irritation by subsequent application of acidic or irritant materials. Such results have been confirmed by in vivo testings against a previously acknowledged superior shaving cream.

In accordance with the present invention a pressurized foaming shaving composition in a valved container that is adapted to maintain the composition under pressure and dispense it when desired, upon opening of the valve thereof, comprises an aqueous, medium, an anionic surface active foaming agent, a foam stabilizer, a mixture of higher fatty acid triglycerides of acids of 16 to 18 carbon atoms, including stearic acid, oleic acid and palmitic acid in which the proportion of saturated fatty acid groups to unsaturated fatty acid groups is about one or more, and an organic liquefied gas propellant to pressurize the composition in the container and aid in discharging it therefrom. The invention also includes a method of preparing such a composition by making a base shaving composition including anionic surface active foaming agent and admixing with it the mixture of higher fatty acid triglycerides of acids of 16 to 18 carbon atoms, including stearic acid, oleic acid and palmitic acid, in which the proportion of saturated fatty acid groups to unsaturated fatty acid groups is about one or more and pressurizing with the organic liquefied gas propellant. The invented compositions may be self-heating, if desired, but although such products soften hairs more quickly, they are not necessary for the attainment of the desired results of this invention, and usually the present products are preferred.

The major constituent of the present shaving composition is an aqueous medium in which the other components are dissolved, emulsified or dispersed. It also often functions as a reaction medium and to some extent may participate in reactions, the principal of which is the neutralization of soap or other synthetic detergent acid(s). Minor proportions of solvents may be present in the medium, as may be dissolved salts, usually in small or trace quantities but it is preferred that the aqueous medium be water alone or essentially water. To avoid objectionable reactions during manufacture or storage and to maintain a desired whiteness or other color in the product the presence of dissolved material such as inorganic salts will preferably be minimized. Thus, distilled or preferably, deionized water, having a content of dissolved materials below five parts per million and preferably below two parts per million, most preferably below one part per million, will be used for the best products. The various solvents that may be present in the aqueous medium are usually limited to the extent of no more than 20% of the water content, preferably less than 10% and most preferably less than 5% but usually no solvents will be present. Among acceptable solvents may be named the lower alcohols, such as those of 1 to 4 carbon atoms, preferably those of 2 to 3 carbon atoms, e.g., ethanol.

To produce the desired foam a surface active foaming agent will be employed. Because nonionic and cationic foaming agents usually produce a lacy or unstable foam and because amphoteric surface active compounds are not as readily available, are more expensive and produce generally inferior foams, the preferred foaming materials will be anionic surface active compounds, such as the anionic detergents. Of these, the higher fatty acid soaps are preferable, especially those in which the soap-forming metal is an alkali metal so that the soaps made are water soluble. However, amine and alkanolamine soaps, e.g., triethanolamine stearate, may also be employed. The water soluble soaps may be prepared by the saponification of fatty acids, natural oils and fats mixtures thereof. The higher fatty acids are those of 12 to 18 carbon atoms and may be saturated or monoolefinic. Very small proportions of diolefinic higher fatty acids, such as linoleic acid, may be saponified but the percentages of di-, tri- and polyolefinic fatty acids present will normally be less than 10% and preferably less than 1% of the fatty acid content from which the soaps are produced. Preferably the higher fatty acid soaps will be mixed sodium and potassium soaps of mixed stearic, palmitic and coconut oil fatty acids; in other words, the higher fatty acid soaps will be essentially saturated soaps. The proportion of potassium soap will be greater than that of sodium soap and the proportion of the total of the stearic acid and palmitic acid soaps will be greater than that of coconut oil soap. The ratio of potassium to sodium will be from about 3:1 to 5:1, preferably about 4:1 and the proportion of the total of stearic and palmitic acid soaps to coconut oil fatty acid soaps will be from 5:1 to 10:1, preferably about 7:1. The proportion of palmitic soap to stearic soap will usually be in the range of 1:5 to 2:1, and most preferably is that in double pressed stearic acid. The described soaps will usually be made by the reaction of corresponding alkali metal hydroxides and free fatty acids or sources thereof and the proportions employed will usually be stoichiometric or, for slight superfatting, with a slight excess of the free fatty acids, such an excess usually being less than 10% and preferably less than 5% of the fatty acids charged. phosphonates In addition to the higher fatty acid soaps other synthetic anionic organic detergents may be utilized. In some cases these will be employed in partial replacement of the soaps and in other instances may completely replace the soaps, although the latter procedure is not preferred. The synthetic anionic detergents will usually include a higher aliphatic or alkyl moiety, preferably linear, and preferably terminally joined to the hydrophilic moiety which will most frequently be a sulfuric or sulfonic acid salt, with the salt-forming ion being alkali metal, ammonium or di- or tri-lower alkanolamine, wherein the lower alkanolamine is of 1 to 4 carbon atoms. Among the useful anionic detergents are the higher alkyl sulfates, higher alkyl sulfonates, higher alkyl benzene sulfonates, ethoxylated higher fatty alcohol sulfates, monoglyceride sulfates, higher fatty acid amides of amino-lower carboxylic acids, such as sodium lauroyl sarcoside, phosphates and phosphonates corresponding to the above mentioned sulfates and sulfonates, and sulfates and sulfonates of the well-known nonionic surface active agents, such as those of polyoxyethylene glycols, of block copolymers of ethylene oxide and propylene oxide, chain terminated with propylene glycol and of polyethoxylated middle alkyl phenols. The above listing is only illustrative and additional listings of suitable synthetic anionic detergents and surface active agents which are useful in the present compositions may be found in the text *Detergent and Emulsifiers* 1969, by McCutcheon and in *Surface Active Agents and Detergents*, Vol. II (1958) by Schwartz, Perry and Berch. Specific examples of useful anionic synthetic organic detergents or surface active agents for inclusion in this formula are: triethanolamine lauryl sulfate; linear dodecyl benzene sodium sulfonate; potassium coconut oil monoglyceride sulfate; ammonium paraffin sulfonate; and ammonium polyoxyethylene stearyl alcohol sulfate.

Although the foaming agent in aqueous medium will produce a foam, in many cases such a foam collapses too quickly and allows the hair which was intended to be softened with moisture after wetting with the surface active (detergent, too) foaming agent to be dried out, whereby shaving is made more difficult. Accordingly, a foam stabilizer or mixture of such stabilizers is employed. Such materials may include organic gums and colloids, serving as thickening agents to maintain the foam in the shape in which it was applied but it will often be found preferable to utilize the lower alkanolamides of higher fatty acids for this purpose. The best of these is lauric myristic diethanolamide wherein the fatty acid of the amide is a mixture of lauric and myristic acids, usually in a proportion of 1:3 to 3:1 and preferably about 1:1. Thus, such material is really a mixture of two different diethanolamides but is generally named for convenience as lauric myristic diethanolamide or LMDEA. Other dialkanolamides of higher fatty acids are also acceptable foam stabilizers. These are diethanolamides of fatty acids of 12 to 18 carbon atoms, preferably of saturated fatty acids, and of mixtures thereof. Of such fatty acids, lauric, myristic, palmitic and stearic acids are most preferred. The lower alkanols may be of 1 to 4 carbon atoms, preferably of 1 to 3 carbon atoms and most preferably of 2 to 3 carbon atoms, e.g., ethanol and isopropanol. In addition to the dialkanolamides, corresponding monoethanolamides are also useful, to a lesser extent. In such compounds the higher fatty acid and lower alkanol moieties may be the same or mixed. Examples of such other foam stabilizers include coconut oil fatty acids monoethanolamide; hydrogenated tallow fatty acids diisopropanolamide; lauric di-n-propanolamide and stearic monoethanolamide. There may be mixed with such materials the known thickening agents such as the natural and synthetic organic gums, e.g., carageenan, gum tragacanth, alginates, gelatin, sodium carboxymethyl cellulose, polyvinyl alcohol and polyvinyl pyrrolidone. It has been found that in the present compositions additional foam stabilizing effects may be obtained by the inclusion of short chain diols and/or triols. Of these, the most useful are propylene glycol and glycerol, with the former being preferred. Sorbitol can also be present.

The mixture of higher fatty acid triglycerides utilized to improve shaving ease and to leave the skin softer, conditioned and more comfortable is principally a mixture of higher fatty triglycerides of acids of 16 to 18 carbon atoms, such fatty acids including stearic acid, oleic acid and palmitic acid. The proportion of saturated fatty acid groups to unsaturated fatty acid groups in the triglycerides will be about one or more, usually being from about 1.1 to 2 and preferably about 1.2 to 1.5. The triglycerides may be obtained directly from natural sources, such as theobroma oil, or may be compounded from individual constituents. The triglycerides may be of a single higher fatty acid, such as tristearin, triolein and tripalmitin but usually and preferably will be of mixtures thereof, such as those found in preferred natural products, such as the oil previously mentioned or which are statistically ascertained from the proportions of the higher fatty acids present in the triglycerides. The proportions which are especially useful are from 25 to 40 parts of stearic acid, 35 to 50 parts of oleic acid and 20 to 30 parts of palmitic acid. A suitable narrower range is 31 to 33 parts of stearic acid, 43 to 45 parts of oleic acid and 23 to 25 parts of palmitic acid. The glycerides of the described fatty acids will often be about 30 to 60% (52) of oleopalmitostearin; 5 to 10% (6) of oleodipalmitin; 15 to 40% (19) of oleodistearin; 10 to 15% (12) of dioleostearin; and 3 to 10% (9) of dioleopalmitin. The numbers after the percentages represent percentages in a specific useful product. Fatty acid contents for such a glyceride mixture may be 35 parts stearic acid, 38 parts oleic acid and 24 parts palmitic acid. Natural products vary in constitution and although the analyses given are average values, proportions may be changed within the given ranges and acceptable shaves are still obtainable. Minor proportions of diglycerides and monoglycerides may be present with the triglycerides but usually will total less than 10% of the total glyceride content and preferably will be absent. However, from 1 to 5% of palmitostearin is sometimes present when theobroma oil is used. The proportion of other fatty acids therein than those named of 16 to 18 carbon atoms is very small or negligible, although some linoleic and arachidic acids may occur in very minor proportion in natural sources of the other acids. The mixture of glycerides mentioned will usually have an iodine value of about 30 to 40 and a melting point of 30° to 35° C., close to normal skin temperature, which assist its conditioning action.

The described triglyceride mixtures are highly preferable constituents of the present shaving composition and are desirably employed either alone or with a minor proportion of a suitable vegetable oil, such as coconut oil, to have the best effect on the shaving cream and on the shaved skin. However, the may be partially replaced by various other mixtures of higher fatty esters, such as the proplylene glycol diesters of U.S. Pat. No. 2,993,063; the palm oil derivatives of U.S. Pat. No. 2,975,063; the lard fractions of U.S. Pat. No. 2,975,061; and the tallow fractions of U.S. Pat. No. 2,975,062. Also, natural sources of similar materials can be used, such as Borneo tallow, Shea butter and Mowrah fat. Generally such replacements will be limited to minor proportions, preferably less than 25% and more preferably less than 10%.

The remaining required constituent of the present compositions is a propellant material to pressurize the container and to assist in discharging the foaming shaving composition. A wide variety of such propellants is known in the aerosol industry, including carbon dioxide, nitrogen, nitrous oxide, argon, air and other inorganic or inert gases but to obtain the desired uniformly foaming compositions of the present invention, which are satisfactorily stable on storage and do not separate so objectionably that light shaking of the container will not disperse them, the organic liquefied gases are used. These materials are lipophilic and aid in solubilizing the various constituents of the compositions, including, especially, the triglyceride mixture thereof. Also, when discharged as a foam onto the skin they tend to deposit a thin film of the triglycerides on the skin and the hairs being shaved, which action aids in creating a smooth shave and leaving the skin softer, more comfortable and conditioned after completion of shaving. It also aids in preventing irritation of the skin by application of any acidic or irritant materials subsequently.

The lower hydrocarbon or lower halogenated hydrocarbon liquefied gas propellants, which are usually emulsified into the aqueous phase by means of the foaming agent and help to maintain the triglycerides dissolved and/or emulsified, too, are those of 1 to 4 carbon atoms, preferably, with respect to the unhalogenated hydrocarbons, of 3 to 4 carbon atoms and, with respect to the halogenated hydrocarbon, of 1 to 3 carbon atoms. The hydrocarbons include n-butane, isobutane and propane and preferably are employed as a mixture of isobutane and propane, most preferably containing about 80 to 90 parts of isobutane and 10 to 20 parts of propane, with the preferable ratio being about 7:1. The halogenated hydrocarbons are preferably those in which the halogen is flourine and/or chlorine, with brominated compounds also being useful. Most preferably, the halogenated propellants include fluorine in the molecule. Exemplary of such materials are monochlorofluoromethane, dichlorodifluoromethane, trichlorodifluoroethane, dichlorotetrafluoroethane, monochlorotetrafluoroethane, trichloromonofluoromethane, tetrachlorodifluoroethane and similar chlorofluoro-hydrocarbons having 1 to 3 carbon atoms per molecule. Of course, the halogenated hydrocarbons or the hydrocarbons are usually employed in mixtures and mixtures of halogenated and unhalogenated hydrocarbons may also be used. The mixing is normally done to regulate the pressure developed, solubilizing properties, corrrosion prevention, emulsion formation, etc. The pressure developed by such a mixture will usually be 10 to 100 85 lbs./sq. in. and more commonly will be from 20 to 70 or 30 to 60 lbs./sq. in., most preferably about 50 lbs./sq. in. Pressures given are gauge pressures. Normally the propellant employed in mixture will include one having an equilibrium pressure at room temperature greater than 30 lbs./sq. in. and one having an equilibrium pressure at room temperature of less than 30 lbs./sq. in., with more of the latter being used, but other mixtures are also useful in particular circumstances.

In addition to the required and optional constituents of the present compositions described above various adjuvants may also be present to give the product additional desired properties. For example, perfumes are usually employed and colorants may be desirable. Additional emollients, solvents, emulsifiers, suspending agents, buffers, conditioning agents, antioxidants, bactericides, proteins, etc., of known types, may be included in the composition for their particular effects. Lanolin is exemplary of such materials and may be used in place of some of the triglyceride mixture. Like the triglycerides, its components closely resemble the fats and oils of the human epidermis. Normally, total contents of such adjuvants will be less than 10% of the product, preferably less than 5% thereof and most often there will be less than 1% of each present. It will generally be desirable to maintain the pH of the shaving cream in the range of 5 to 10.5, preferably from 7 to 10.5 and this may be done with the aid of buffering materials or control of acid and base contents.

In addition to making the present pressurized foaming shaves, variations of the basic formulation to produce subsequently foaming gel shaves, as described in U.S. Pat. No. 3,541,581 may also be made. Self-heating shaving creams of the types described in U.S. Pat. Nos. 3,326,416 and 3,341,418 may be improved by the inclusion in those formulas of the present triglyceride mixtures, preferably with the additional foaming agent and foam stabilizer. In another variation of the invention, which, however, is not preferred, chemical depilating agents such as thioglycolic acid, sodium thioglycolate, calcium thioglycolate and equivalent materials may be employed together with or in replacement of the foaming agent and the hair may be removed either chemically or by a combination of mechanical and chemical operations. In all such uses, however, it is important to have the triglyceride mixture present, together with solubilizing and foaming propellant, to assist in distributing the triglyceride mixture over the skin and in contact with the hair to be removed.

The proportions of the various constituents in the preferred foaming shaving compositions to obtain superior results are from 70 to 90% of water, 5 to 15% of anionic surface active foaming agent, 0.5 to 3% of foam stabilizer, 1 to 5% of the mixed triglycerides and 1 to 10% of propellant. Preferred ratios include from 75 to 85% of water, 7 to 13% of alkali metal higher fatty acid soap, 0.7 to 1.5% of higher fatty acid dialkanolamides, 2 to 4% of the mixture of higher fatty acid triglycerides and 2 to 7% of propellant mixture. In some compositions it may be desirable to have present 1 to 5% of auxiliary foam stabilizer and emollient, such as propylene glycol, and 0.1 to 0.5% of another emollient, such as coconut oil. The normal percentage of perfume, which may be a mixture of essential oils, perfume aldehydes and ketones and suitable solvents and fixatives, will be from 0.1 to 3%. The proportion of high pressure propellant to low pressure propellant in the mixed propellant system will usually be less than one. In a most preferred foaming shaving composition there will be present about 79% of water, 9% of mixed sodium and potassium soaps of stearic, palmitic and coconut oil fatty acids, 1% of lauric myristic diethanolamide, 2.7% of propylene glycol, 0.3% of coconut oil, 3% of a mixture of triglycerides containing about 32 parts stearic acid, 44 parts of oleic acid and 24 parts of palmitic acid, 1% of perfume and 4% of a mixture of one part of propane and seven parts of isobutane, producing a pressure of about 50 lbs./sq. in. gauge.

The manufacture of the present compositions is easily effected and for the most part standard cosmetic formulating procedures may be employed. However, it is of importance that the mixture of higher fatty acid triglycerides be admixed with an already neutralized anionic surface active foaming agent so as to avoid any undesirable reactions with the triglyceride mixture during a neutralization procedure. Thus, the mixture of higher fatty acid soaps may be produced by the neutralization of higher fatty acids with alkali metal hydroxide in an aqueous medium so long as the higher fatty acid triglyceride mixture is not present during the neutralization reaction. After completion of neutralization the triglycerides may be incorporated with the other components of the shaving composition. The foam stabilizer, e.g., lauric myristic diethanolamide, may be admixed with the soap mixture before addition of the triglyceride or after and similar admixings with the propylene glycol and coconut oil, if present, may be made at any suitable time, with the coconut oil also being limited to post-neutralization additions. For best results, the neutralization and various other mixings will normally be conducted at elevated temperatures, with the temperatures being lowered as the manufacturing proceeds and the more volatile materials are added, so as to avoid losses thereof. For example, perfumes will normally be added last and at such time the temperature of the composition will preferably be only slightly above room temperature.

In the usual procedure followed for producing the present compositions a mixture of potassium and sodium hydroxide is dissolved in low hardness water, preferably deionized water, and there is admixed with it a molten mix of stearic, palmitic and coconut oil fatty acids, with both the aqueous and the lipophilic materials being at elevated temperatures so that the reaction mixture is in the 60° to 90° C. range. After completion of neutralization the higher fatty acid dialkanolamide and mixed higher fatty acid triglyceride are admixed with the neutralized anionic foaming agent made, with the temperature of the product at the stage being in the range of 40° to 70° C. Subsequently the perfume and other materials may be added at a temperature in the range of 20° to 50° C. The procedure may be varied to have stable materials added at an earilier stage, if desired. Generally, it is preferred that the coconut oil and propylene glycol, if present, be added with the triglyceride mixture after neutralization of the soap or other anionic surface active agent or detergent. After the final addition and completion of preparation of the emulsion, the product may be cooled or may be directly added to a pressure container and the propellant may be added thereto, usually through the dispensing valve. The product may be shaken in the container to aid in emulsifying the propellant with the other constituents but often this is not necessary since the force of addition of the gas and the normal mixing in transit, etc., produce the emulsion.

The following examples illustrate but do not limit the invention. Unless otherwise indicated, temperatures are in ° C. and parts are by weight.

EXAMPLE 1

| | Parts by Weight |
|---|---|
| Deionized water (dissolved salt content less than 1 p.p.m. | 79.51 |
| Stearic acid, double pressed | 7.16 |
| Coconut oil fatty acids | 1.00 |
| Lauric myristic diethanolamide | 1.00 |
| Propylene glycol | 2.70 |
| Potassium hydroxide, 34.2% aqueous solution | 3.42 |
| Sodium hydroxide, aqueous, 19.1% Na$_2$O content | 0.96 |
| Coconut oil | 0.25 |
| Triglyceride mixture, m.p. = 32° C.; Iodine No. = 35. (fatty acids = 44 parts oleic acid, 32 parts stearic acid and 24 parts palmitic acid) | 3.00 |
| Perfume, floral | 1.00 |

A foaming agent solution is prepared by adding the sodium hydroxide and potassium hydroxide solutions to the deionized water, heating to a temperature of about 75° C. and admixing with such caustic solution a previously heated melt of double pressed stearic acid and coconut oil fatty acids, with care being taken that the exotherm does not raise the temperature over 90° C. After completion of the addition of the fatty acids, which are in approximately stoichiometric quantity, with a slight excess thereof present, the higher fatty acid soaps have been manufactured. The aqueous solution thereof is then cooled to a temperature of about 55° C., at which the propylene glycol, lauric myristic diethanolamide, coconut oil and mixed triglycerides are added. The mix is then cooled to about 35° C. and the perfume is admixed therewith, after which cooling to room temperature, about 20° to 25° C. is effected. The product made is added to valved aerosol containers of 6 and 12 oz. sizes and four proportions of a mixture of 3½ parts of isobutane and ½ part propane are added to 100 proportions of the rest of the composition (150 grams total weight in the 6 oz. containers and 300 grams/12 oz. container) in the containers through the valves thereof, after which the containers are shaken to aid in producing an emulsion. They are then packed and are ready for shipment and use.

Before use, the container is shaken slightly and the valve button is depressed, allowing dispensing of a desired amount of shaving foam through the dispensing spout. Such foam is applied to the faces of humans panelists testing the product against a standard commercially successful and highly regarded aerosol shaving cream formulation. The panelists apply the experimental shaving foam to one side of the face and the control foam to the other and shave and compare. In such tests they report that the experimental shaving cream gives a more comfortable and closer shave and leaves the skin feeling soft, relaxed (not taut) and conditioned.

When the experimental shaving foam is used for shaving of female legs and axillae comfortable shaves are obtained and less skin irritation results than with various other commerical shaving products. Also, when commerical antiperspirant compositions containing aluminum chlorhydroxide or aluminum chloride are sprayed onto the skin or otherwise applied thereto, as by roller or pad application of antiperspirant lotion, liquid, emulsion or cream, after shaving, there is less irritation after use of the present shaving product than after use of ordinary aerosol lather shave creams. In both the shaving of whiskers from the male face and shaving of hair from female legs and axillae the cream applied has sufficient body so as not to collapse and dry out before shaving is complete.

In other experiments the foaming shaving composition applied is heated, either after exiting from the container or by co-dispensing with the contents of the container an exothermic mixture of an organic reducing agent, such as sodium sulfinate or a suitable thioglycol with an oxidizing agent, such as an aqueous hydrogen peroxide solution. The heated shave cream resulting has sufficient body to maintain moisture in contact with the hair or whiskers during the shave and waiting time before shaving is diminished due to the softening effect of the heated surface active material in contact with the hair and whiskers. Again, the experimental product is superior to the control product in shaving characteristics and in comfort and skin feel after shaving.

In variations of the above formula the triglyceride mixture concentration is changed, so that ½, 1, 2, 4, 5 and 6 parts thereof are included in various other "experimental" formulations. With only ½% of the triglycoride mixture present, little or no difference is noted between the properties of the experimental and control formulations and with 6% of the mixture present the shaving cream is to thin to be acceptable. It appears that the 3% concentration is the best, with more than 3% having an improved effect on the feel of the skin after shaving but also serving to thin somewhat the foam produced, whereas with less than 3%, undesirable foam effects are not obtained but conditioning action of the product on the skin is also diminished.

EXAMPLE 2

The formula of Example 1 is modified by deletion therefrom of the propylene glycol and coconut oil constituents. The product obtained, when tested in the manner described in Example 1, is still superior to control shaving creams but the foam does not have as much body nor is it as stable as before the formula change and some users can detect a diminution in softness of the skin and conditioning properties of the foam. When the soaps charged are changed so that a major proportion of the soap content is of sodium soap is not as satisfactory in the respects described as that wherein potassium soap is the predominant soap present. Also, when the soap is changed to an all-stearic acid soap or all-coconut oil fatty acid soap, less satisfactory shaving creams are produced. When the triglyceride mixture is changed to approximate that of tallow, coconut oil or mixtures thereof, conditioning and softening qualities of the shaving cream are diminished. However, when instead of utilizing a mixture of the particular triglycerides produced by blending olein, stearin and palmitin and/or mixed triglycerides from the same acids, a natural material (theobroma oil or cocoa butter) is employed, equivalent results are obtained. Also, when the materials of the previously mentioned U.S. patents are substituted to the extent of 5 to 20% for the mixed triglycerides, good products, like those experimental products previously described, are obtained.

EXAMPLE 3

The formula and procedure of Example 1 are followed with the exception that in place of the lauric myristic diethanolamide, palmityl isopropanolamide is used. With this foam stabilizer the foams produced are of lesser body but good shaving and conditioning of the skin are obtainable.

In modifications of this experiment, in place of the propellant a mixture of Propellants 11 and 12 in 3:2 ratio is employed. No significant difference in the properties of the foam occur due to such change. Also, when the perfume is omitted no change in properties of the product is noted.

The invention has been described with respect to examples and illustrations thereof but is not be limited to them because it is evident that one of skill in the art, with the present invention before him, will be able to utilize substitutes and equivalents without departing from the spirit or scope of the invention.

What is claimed is:

1. A pressurized foaming shaving composition in a valved container that is adapted to maintain the composition under pressure and dispense it when desired, upon opening of the valve thereof, which comprises water, an anionic surface active foaming agent, a foam stabilizer, 1 to 5 percent of a mixture of higher fatty acid triglycerides of acids of 16 to 18 carbon atoms, including 25 to 40 parts of stearic acid, 35 to 50 parts of oleic acid and 20 to 30 parts of palmitic acid in which the proportion of saturated fatty acid groups to unsaturated fatty acid groups is about one or more, and an organic liquefied gas propellant to pressurize the composition in the container and to aid in discharging it therefrom.

2. A pressurized foaming shaving composition according to claim 1 wherein the anionic surface active foaming agent is a higher fatty acid soap having from 12–18 carbon atoms, the foam stabilizer is a higher fatty acid alkanolamide wherein the fatty acid has from 12–18 carbon atoms and the alkanol has from 1–4 carbon atoms, and the organic liquefied gas propellant is a mixture of such propellant compounds selected from the group consisting of lower hydrocarbons and halogenated lower hydrocarbons wherein the halogens are selected from the group consisting of chlorine, bromine and fluorine.

3. A pressurized foaming shaving composition according to claim 2 wherein the water is of low hardness, the anionic surface active foaming agent is an alkali metal higher fatty acid soap or mixture thereof, the foam stabilizer is a higher fatty acid dialkanolamide or mixture thereof, the mixture of higher fatty acid triglycerides is a mixture of triglycerides containing 31 to 33 parts of stearic acid, 43 to 45 parts of oleic acid and 23 to 25 parts of palmitic acid, with the proportion of saturated higher fatty acid groups to unsaturated higher fatty acid groups in such triglycerides being 1.2 to 1.5, and the organic liquefied gas propellant is capable of generating a pressure of 10 to 100 lbs./sq. in. in the composition.

4. A pressurized foaming shaving composition according to claim 2 comprising 70 to 90% of water, 5 to 15% of higher fatty acid soap, 0.5 to 3% of higher fatty acid alkanolamide, 2 to 4% of the mixed triglycerides, and 1 to 10% of propellant.

5. A pressurized foaming shaving composition according to claim 3 comprising from 75 to 85% of low hardness water, 7 to 13% of alkali metal higher fatty acid soap(s), 0.7 to 1.5% of higher fatty acid dialkanolamide(s), 2 to 4% of the mixture of higher fatty acid triglycerides and 2 to 7% of propellant mixture.

6. A pressurized foaming shaving composition according to claim 5 comprising 75 to 85% of deionized water, 7 to 13% of mixed sodium and potassium soaps of stearic, palmitic and coconut oil fatty acids, with the proportion of potassium soap being greater than that of sodium soap and the proportion of the total of stearic acid and palmitic acid soaps being greater than that of coconut oil fatty acid soap, 0.7 to 1.5% of a mixed higher fatty acid dialkanolamide, 1 to 5% of propylene glycol, as a supplemental foam stabilizer and emollient, 2 to 4% of the mixture of higher fatty acid triglycerides, 0.1 to 0.5% of coconut oil, as an emollient, 0.1 to 3% of perfume and 2 to 7% of propellant mixture, which mixture includes propellants which have equilibrium pressures at room temperature greater than 30 lbs./sq. in. gauge and less than 30 lbs./sq. in. gauge, respectively, and in which the proportion of high pressure propellant to lower pressure propellant is less than one.

7. A pressurized foaming shaving composition according to claim 6 which consists essentially of about 79% of water, 9% of mixed sodium and potassium soaps of stearic, palmitic and coconut oil fatty acids, in which the proportion of potassium to sodium is about 4 to 1 and the proportion of the total of stearic and palmitic acid soaps to coconut oil fatty acid soap is about 7 to 1, 1% of lauric myristic diethanolamide, 2.7% of propylene glycol, 0.3% of coconut oil, 3% of a mixture of triglycerides containing about 32 parts stearic acid, about 44 parts of oleic acid and about 24 parts of palmitic acid, 1% of perfume and 4% of a mixture of one part of propane and 7 parts of isobutane, at a pressure of about 50 lbs./sq. in. gauge.

8. A composition as defined in claim 1 wherein said anionic surface active agent is selected from the group consisting of a higher alkyl sulfate, a higher alkyl sulfonate, a higher alkyl benzene sulfonate, an ethoxylated higher fatty alcohol sulfate, a mono-glyceride sulfate, higher fatty acid amide of amino-lower carboxylic acid.

9. A composition as defined in claim 1 wherein said foam stabilizer is selected from the group consisting of a natural organic gum, a synthetic organic gum a colloid, a higher fatty acid alkanolamide wherein the fatty acid has from 12 to 18 carbon atoms and the alkanol has from 1 to 4 carbon atoms.

10. A composition as defined in claim 9 wherein said foam stabilizer is a mixture of lauric and myristic acids in a proportion of about 1:3 to 3:1.

11. A method of preparing a pressurized foaming shaving composition in a valved container according to claim 1 which comprises preparing a base shaving composition including anionic surface active foaming agent and admixing with it said mixture of higher fatty acid triglycerides of acids of 16 to 18 carbon atoms.

12. A method according to claim 8 wherein the anionic surface active foaming agent is a mixture of higher fatty acid soaps having from 12–18 carbon atoms, such soaps are produced by the neutralization of higher fatty acids with alkali metal hydroxide in an aqueous medium, after such neutralization the mixture of higher fatty acid triglycerides of acids of 16 to 18 carbon atoms is admixed with the soap mixture in an aqueous medium and the resulting emulsion is pressurized in the valved container by addition to it of an organic liquefied mixture of propellant compounds selected from the group consisting of lower hydrocarbons and lower halohydrocarbons.

13. A method according to claim 9 wherein low hardness water with a mixture of potassium and sodium hydroxide dissolved therein is heated and has admixed and reacted with the hydroxide a mixture of stearic, palmitic and coconut oil fatty acids in the molten state in such proportion that the total quantity of stearic acid and palmitic acid soaps is greater than that of coconut oil fatty acid soap and with the proportions of the fatty acids and alkali metal hydroxide being about stoichiometric, and there are admixed with the soap mixture produced a higher fatty acid dialkanolamide, the mixed higher fatty acid triglycerides and perfume and the mixture produced is pressurized in the container by addition of a propellant mixture in which the components are selected from the group consisting of lower hydrocarbons and chloro-fluoro-lower hydrcarbons and fluoro-lower hydrocarbons capable of generating a pressure of from 10 to 100 lbs./sq. in. in the container.

* * * * *